(12) United States Patent
Chan

(10) Patent No.: US 6,627,058 B1
(45) Date of Patent: Sep. 30, 2003

(54) THICK FILM CONDUCTOR COMPOSITION FOR USE IN BIOSENSORS

(75) Inventor: Man-Sheung Chan, Chapel Hill, NC (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 318 days.

(21) Appl. No.: 09/761,311

(22) Filed: Jan. 17, 2001

(51) Int. Cl.$^7$ .................. G01N 27/327; B22F 1/00; H01B 1/04

(52) U.S. Cl. ............. 204/403.15; 204/294; 252/503; 419/32

(58) Field of Search ................ 252/503, 514; 419/32; 204/292, 294, 403.01, 403.1, 403.11, 403.15, 416

(56) References Cited

U.S. PATENT DOCUMENTS

| | | | |
|---|---|---|---|
| 3,539,455 A | | 11/1970 | Clark et al. |
| 4,081,423 A | | 3/1978 | Hardenfelt |
| 4,970,145 A | | 11/1990 | Bennetto et al. |
| 5,089,173 A | * | 2/1992 | Frentzel et al. ............ 252/514 |
| 5,160,416 A | | 11/1992 | Cawlfield et al. |
| 5,160,418 A | | 11/1992 | Mullen |
| 5,378,628 A | | 1/1995 | Gratzel et al. |
| 5,616,222 A | | 4/1997 | Maley et al. |
| 5,643,721 A | * | 7/1997 | Spring et al. .................. 435/6 |
| 5,653,918 A | | 8/1997 | Towlson |
| 5,707,502 A | | 1/1998 | McCaffrey et al. |
| 5,855,820 A | * | 1/1999 | Chan et al. ................. 252/511 |
| 6,042,751 A | | 3/2000 | Chan et al. |
| 6,228,288 B1 | * | 5/2001 | Chacko ..................... 252/511 |

FOREIGN PATENT DOCUMENTS

| | | |
|---|---|---|
| EP | 0 757 246 A2 | 2/1997 |
| EP | 0 942 278 A2 | 9/1999 |
| EP | 0987333 A | 3/2000 |
| WO | WO 98/20331 | 5/1998 |
| WO | WO 9910520 A | 3/1999 |

OTHER PUBLICATIONS

Pages 214 and 503 of the Industrial Solvents Handbook, 5$^{th}$ Ed., ed. Ernest Flick.*
Frew et al., "Electrochemical Biosensors," Analytical Chemistry, 1987, 933–944, 59, American Chemical Society, USA Aug.
Michael Pishko, "Macromolecular 'Wiring' of Oxidoreductases and Potential Interesting Applications," TRIP, 1995, 342–347, 3, Elsevier Science Ltd. Oct.
Ikeda et al., "Electrocatalytic Oxidation of D–Gluconate at a Ubiquinone–Mixed Carbon Paste Electrode with an Immobilized Layer of D–Gluconate Dehydrogenase from Bacterial Membranes," Agric. Biol. Chem., 1987, 747–754, 51.
Mizutani et al., "Amperometric Enzyme Sensor for Glucose Use of Glucose Oxidase and Carbon Paste Electrode Modified with Catalyst for Hydrogen Perioxide Oxidation," Cygnus, Inc., 1992, 1141–1142, 60.
Wring et al., "Chemically Modified, Carbon–based Electrodes adn Their Application as Electrochemical Sensors for the Analysis of Biologically Important Compounds,"Analyst, 1992, 1215–1229, 117 Aug.

(List continued on next page.)

Primary Examiner—Nam Nguyen
Assistant Examiner—Alex Noguerola

(57) ABSTRACT

This invention is directed to a composition comprising: (a) platinum group metal powder, alloys, or mixtures thereof as a powder or deposited on graphite supports; (b) poly(glycol ether), derivatives, or mixtures thereof; (c) carbon-based electrically conductive filler; and (d) thermoplastic polymer or mixtures thereof. The invention is further directed to a process for dispersing platinum group metal powder, alloys, or mixtures thereof in poly(glycol ether), derivatives, or mixtures thereof. The invention is further directed to the above composition wherein the platinum group metal powder has been dispersed according to the above process.

17 Claims, 1 Drawing Sheet

OTHER PUBLICATIONS

Tamada et al., "Measurement of glucose in diabetic subjects using noninvasive transderman extraction," Nature Medicine, 1995, 1198–1200, 1 Nov.

Tierney et al., "In Vivo Performance of a Continual, Transderman Glucose Monitoring System," Preprint from TRP Oak Ridge Conference, 1998.

Gorton, "A Carbon Electrode Sputtered with Palladium and Gold for the Amperometric Detection of Hydrogen Peroxide," Analytica Chimica Acta., 1985, 247–253, 178, Elsevier Science Publishers B.V., The Netherlands.

Linke et al., "Amperiometric biosensor for in vivo glucose sensing based on blucose oxidase immobilized in a redox hydrogen," Biosensors & Bioelectronics, 1994, 151–158, 9, Elsevier Science Publishers Ltd.

Guilbault et al., "An Enzyme Electrode for the Amperometric Determination of Glucose," Anal. Chim. Acta., 1973, 439–455, 64, Elsevier Scientific Publishing Company, The Netherlands.

Henning et al., "Biosensors for Personal Diabetes Management," Chemical Analysis, 1998, 3–46, 148, John Wiley & Sons, Inc., New York.

Cass et al., "Ferrocene–mediated Enzyme Electrode for Amperometric Determination of Glucose," Analytical Chemistry, 1984, 667–671, 56, No. 4, Americal Chemical Society, USA.

* cited by examiner

THICK FILM CONDUCTOR COMPOSITION FOR USE IN BIOSENSORS

FIELD OF INVENTION

This invention relates to an improvement in polymer thick film (PTF) compositions containing platinum group metal catalysts, a catalyst enhancing additive, graphite or conductive carbon fillers, and a thermoplastic binder. The improved PTF conductor compositions can be used in printing sensing/working electrodes for electrochemical biosensors based on hydrogen peroxide detection. Electrochemical biosensors, which are combinations of an electrochemical sensor and a biomolecule recognition element are useful in the analysis of biological analytes such as glucose, cholesterol, creatinine, alcohol, uric acid, and lactate in body fluid, and are therefore useful in the field of medical devices and analytical instruments for medical diagnostics.

BACKGROUND OF THE INVENTION

The majority of electrochemical biosensors fall within two categories (1) metal-catalyzed electrochemical biosensors or (2) electron-transfer mediator modified electrochemical biosensors. For example, a metal-catalyzed glucose sensor detects the hydrogen peroxide by-product which is produced in a one-to-one ratio from glucose through an enzyme-catalyzed air oxidation process, such as:

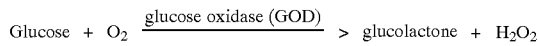

U.S. Pat. No. 3,539,455 (1970) by Clark discloses a platinum based glucose sensor useful for determination of blood glucose in diabetics. Guilbault and Lubrano (1973) reported amperometric biosensors having platinum electrodes with an immobilized-enzyme suitable for glucose sensor applications. Mizutani et al. (1992) reported a platinum/carbon paste (CP) composition with a 1/9 Pt/C ratio suitable for making glucose sensors. U.S. Pat. No. 4,970,145 (1990) to Bennetto et al. discloses a biosensor with a porous enzyme electrode comprising platinized carbon paper having a fluoropolymer binder. These platinum/carbon-based biosensors have sensitivity for detection of glucose only at concentrations of millimolar (mM) glucose with an electric current response of <20 $\mu A/cm^2 \cdot mM$ glucose. U.S. Pat. No. 5,160,416 (1992) to Mullen et al. discloses an enzyme electrode produced by coating a water based suspension consisting of platinized carbon or graphite particles and enzyme. U.S. Pat. No. 5,616,222 (1997) to Maley et al. discloses a sensor working electrode comprising platinized carbon particles, enzyme, protein, and polymer binder. These enzyme-containing compositions require the coating be done at temperature well below the enzyme deactivation temperature, typically below 60° C., and are not suitable for high throughput sensor manufacturing processes. Furthermore, these enzyme electrodes have high metal loading, typically 5–15% Pt by weight of total carbon/graphite. A working electrode with high loading of platinum group metal can lead to high material cost and unacceptably high loss of hydrogen peroxide due to metal-catalyzed decomposition of hydrogen peroxide. Patent Application WO 98/20331 disclosed ink compositions useful for printing a working electrode comprised of platinum group metal catalyst deposited on graphite and carbon black filler in a cross-linked bonded matrix. A printing ink based on a thermoset polymeric binder would require long curing time to form a cross-linked matrix, and therefore making it unsuitable for low cost high throughput sensor fabrication processes. For single-use disposable biosensors, it is critical that catalyst printing ink for the working electrode be low cost and suitable for low cost and high throughput sensor fabrication processes.

There remains a need for electrochemical sensor materials with much improved sensor performance of high catalytic activity/current response and low background current noise to expand the capability of $H_2O_2$-based biosensors for monitoring biological analytes at the micromolar ($\mu M$) level and to assure a high confidence of detecting low level of analytes in body fluids. One example demonstrating the need of such a high performance biosensor was given by Tamada, Bohannon, and Potts (1995) who reported the iontophoretic extraction of body fluid, which can be used in non-invasive glucose monitoring. The body fluid can then be analyzed in situ for glucose levels and thus provide a method for non-invasive monitoring of glucose. The glucose concentration in the extracted body fluid is typically in the micro-molar level, which produces electric current in the nanoampere (nA) level, and thus requires a biosensor with low detection limit of glucose determination. A key limiting factor which affects the glucose detection limit is electrochemical signal noise, background current, which may be from electrochemically active impurities, temperature fluctuation, or from many other sources. It is desirable that biosensors have low background current, which also does not change much with temperature fluctuation.

To achieve high catalytic activity of a catalyst ink composition, catalyst particles in the composition, either as dispersed particles or as deposited particles on carbon/graphite support, may have very small size and large total surface area. Commercially available platinum metal black powders are agglomerates of nanoparticles having average particle size of <100 nm. To achieve high activity, these metal powders may be further dispersed into a fine dispersion before used in a PTF ink composition. There remains a need for a process to produce very fine, stable platinum group metal dispersions having dispersed particle size of <100 nm for uses in PTF compositions.

SUMMARY OF INVENTION

This invention is directed to a composition comprising: (a) platinum group metal powders, alloys, or mixtures thereof as a powder or deposited on graphite supports or mixtures thereof; (b) poly(glycol ether), derivatives, or mixtures thereof; (c) carbon-based electrically conductive filler; and (d) thermoplastic polymer or mixtures thereof.

The invention is further directed to a process for dispersing platinum group metal powder, alloys, or mixtures thereof comprising the steps of mixing the platinum group metal powder, alloys or mixtures thereof with poly(glycol ether), derivatives, and mixtures thereof and using a dispersing means to disperse the platinum group metal powder, alloys and mixtures thereof with the poly(glycol ether), derivatives, and mixtures thereof.

The invention is further directed to the above composition wherein the platinum group metal powders, alloys and mixtures thereof have been dispersed according to the above process.

DETAILED DESCRIPTION OF THE INVENTION

Figure 1:
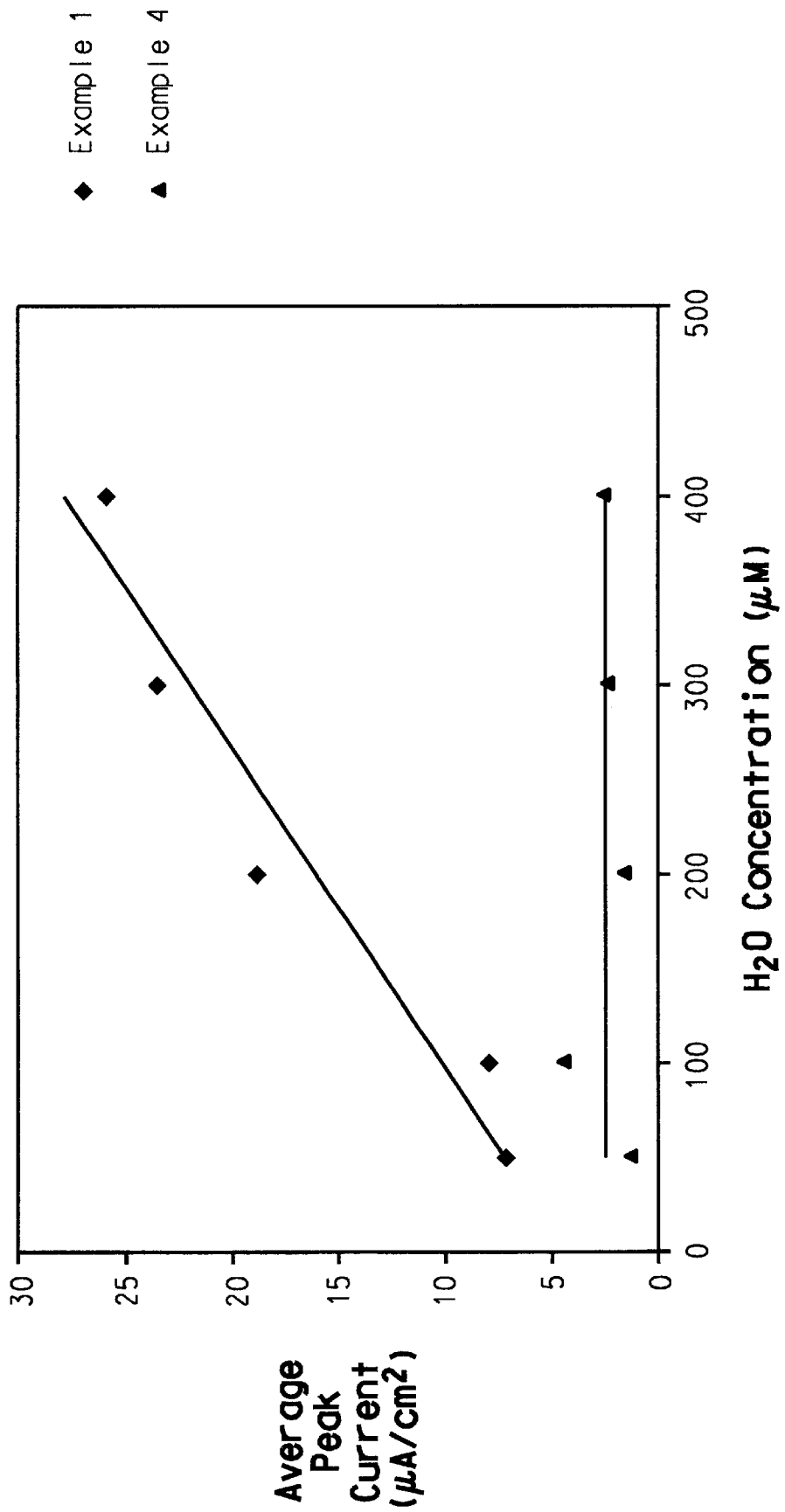
FIG. 1 is a graph of the sensor response to concentration of $H_2O_2$ as described in test C for Example 1 and 4. It demonstrates the effect of PTMEG on sensor performance.

The compositions covered in the present invention can be used in printing sensing or working electrodes in electrochemical biosensor applications, and more specifically, amperometric glucose sensors. The composition can be used to make glucose biosensors with working electrodes with extremely high sensitivity for analysis of glucose at micromolar levels, for example, a method for non-invasive monitoring of analytes transdermally extracted from the body.

The composition has the following characteristics when used as a working electrode:

(a) Printed PTF working electrodes have high electrocatalytic activity toward a target chemical or biomolecule, and therefore provide a strong electrical signal even at extremely low concentrations of the target chemical. Furthermore, the PTF working electrode does not introduce excessive background current signal noise, which would limit the ability of a biosensor to detect low concentrations of a target chemical.

(b) Printed PTF working electrodes have stable and consistent electrocatalytic activity enabling the biosensor to handle multiple analyses for continual glucose monitoring.

(c) The composition can be used in manufacturing of disposable biosensors at low cost.

(d) The composition has rheological properties that facilitate manufacturing of sensors by conventional printing processes.

Through a unique combination of platinum group metal electrocatalysts and carbon-based electronically conductive materials, a low cost electrocatalyst system containing as low as 0.5/99.5 of metal/carbon ratio produces a biosensor working electrode to detect glucose levels of 100 nanomolar. This unique electrocatalyst in combination with a thermoplastic resin solution provides a low cost and reliable metal/carbon-based composition for use in making disposable biosensors.

The composition may include platinum group metal powder, alloys, or mixtures thereof that have been dispersed in poly(glycol ether), its derivatives, or mixtures thereof. This dispersion process can produce metal particles of <100 nm average particle size. Such dispersed particles can produce higher catalytic activity.

The composition comprises the following components: (A) electrocatalyst selected from platinum group metals, alloys, or mixtures thereof, whether as powder, deposited on graphite support, or dispersed in poly(glycol ether), derivatives, or mixtures thereof, (B) carbon-based conductive filler selected from particles of graphite, modified graphite, graphite support, conductive carbon, or mixtures thereof; (C) poly(glycol ether), derivatives, or mixtures thereof, and (D) thermoplastic polymer or mixtures thereof. The composition may also comprise (E) solvent.

Where numbers are stated in the specification and claims, they include all numbers that would be rounded to the stated number using standard rounding techniques. When the ranges of percentage of ingredients are stated as based on solids, they are calculated based on the composition with no solvent added or with any solvent removed. Where surface areas or particle sizes are stated, they are the surface areas or particle sizes of the raw materials before mixing into the composition.

(A) Electrocatalyst

Electrocatalysts may be utilized in the present invention in three forms: (1) platinum group metal powders, (2) platinum group metals deposited on electrically conductive supports, or (3) platinum group metal powders dispersed in poly(glycol ether).

(1) Platinum Group Metal Powders

Platinum group metals are well known for their catalytic activity for organic and inorganic reactions as well as catalytic electrochemical reactions. The invention uses platinum group metals, such as platinum, palladium, rhodium, iridium, ruthenium, osmium, alloys or mixtures thereof.

Some embodiments use platinum as a platinum group metal powder. The metal powder typically has a high surface area (>5 $m^2/g$). Metal powder catalysts such as platinum black are also suitable. Metal powder catalysts with very high surface area (>65 $m^2/g$) tend to increase sensor background current. Platinum black powders having a surface area of 25–60 $m^2/g$, commercially available from Colonial Metals Inc., Elkton, Md. and Alfa Aesar, Ward Hill, Mass., are suitable.

(2) Platinum Group Metals Deposited on Electrically Conductive Supports (Metallized Graphite)

Metallized graphite is platinum group metal particles, alloys, or mixtures thereof directly deposited on support particles. Supported metal catalysts offer electrocatalytic activity through direct electron-transfer from catalytic sites to the conductive network. Graphite is a widely used support particle in electrocatalyst applications. Graphite offers good electrical conductivity and low electrochemical signal interference because of its inertness to electrochemical reaction. Metallized graphite with 0.5–10% metal based weight on graphite is suitable for use as the electrocatalyst. Higher metal loading not only makes sensors more costly for disposable sensor applications but also leads to background current noise due to high activity in catalyzed side reactions. Catalyst particles deposited in microcrystalline size, typically <50 nm produce high catalytic activity and low material cost. Metallized graphite can be prepared using a method described in the U.S. Pat. No. 4,044,193.

(3) Process for Dispersing Platinum Group Metal Powders in Poly(Glycol Ether)

Platinum group metal powders, alloys, or mixtures thereof can be dispersed in poly(glycol ether), derivatives, or mixtures thereof. Finely dispersed metal particles of <100 nm can be achieved. Suitable powders include all those listed hereinabove. The process comprises mixing the metal powder with poly(glycol ether), then using a dispersing means to achieve the desired particle size. The dispersing means can include three-roll milling, high-speed dispersion, power mixing, media milling, mulling, and any other method known to those skilled in the art. The process can also comprise the additional step of mixing inert organic solvent or mixtures thereof with either or both of the poly(glycol ether) and the platinum group metal powder, at any time in the process. In one embodiment poly(glycol ether) is dissolved in aromatic hydrocarbon before mixing with the platinum group metal powder. If a solvent is used in the dispersion process, it can be a different solvent from the solvent used to dissolve the thermoplastic polymer.

In some embodiments the amount of metal whether found as metal powder, metallized graphite, or metal powder dispersed in poly(glycol ether) (referred to collectively as "metal") in the composition is about 0.1–5% wt based on solids. In some embodiments the range is 0.3–3% wt. and in some the range is 1–2.5% wt. In some embodiments the metal/graphite ratio is in the range of 5/95 to 0.5/99.5, wherein the graphite constitutes the total amount of graphite found in the composition whether found as support particles or carbon-based conductive filler as described in part (B) hereinbelow.

(B) Carbon-based Conductive Fillers

Both graphite and conductive carbon are commonly used carbon-based electrically conductive fillers. However, due to their different crystalline and electronic structure, graphite materials have rather different electrical conductivity, and surface chemical structure and electrochemical activity from conductive carbon. Graphite particles typically have extended crystalline domain of >1 μm with stacked layers of continuous $sp^2$ carbon planes. The surface along the $sp^2$ carbon plane, the Basal plane, is electrochemically inert while the edges of the $sp^2$ carbon planes often have oxygenated functional groups making them electrochemically active. On the other hand, conductive carbon particles typically known as carbon black have small crystalline domain with somewhat randomly oriented $sp^2$ planar structures. These differences in microcrystalline surface chemical structure lead to different physical and chemical properties in graphite versus conductive carbon. Typically graphite materials have higher electrical conductivity and lower electrochemical activity than carbon black (see review article by McCreery [1991]).

Graphite material suitable for platinum group metal/carbon-based conductive filler thick film compositions (Pt/C inks) used in working electrodes of printed biosensors includes synthetic, pyrolytic, or natural graphite. Synthetic graphite powders made from petroleum coke that have good balance of low metal impurities (usually <500 ppm metal contamination) and rich surface functional groups are suitable. Suitable graphite materials typically have particles with diameters of 1–30 microns with mean particle diameter in the range of 2–10 micron and a surface area of <20 $m^2/g$. Larger graphite particles tend to cause problems in printing sensors by screen-printing. Fine graphite powders in a platinum group metal/carbon composition tend to have low conductivity and high sensor background current.

The graphite can be modified before addition to the composition to enrich the surface functional groups that interact with electrocatalyst particles. Modified graphite can be prepared by reduction with strong reducing agent and plasma etching processes. Strong reducing agents include sodium hypophosphite, sodium borohydride, sodium bisulfite, and sodium formate. One embodiment of modified graphite can be prepared by stirring 1 part graphite and 6 parts 3% aqueous sodium hypophosphite for 90 minutes at 65° C., filtering, washing with deionized water, and drying at 120° C.

Conductive carbon powders suitable for uses in platinum group metal/carbon ink compositions are conductive carbon black having small particle size and low surface area. Carbon black powders having surface area of <150 $m^2/g$ and average primary particle size of <100 nm are suitable. Such low surface-area carbon black powders can provide platinum group metal/carbon inks with suitable rheology for printing and printed sensors with a good sensor signal/noise ratio. Carbon black powders having high surface area can lead to high background current and make the ink difficult to print. Carbon black powders with surface area <80 $m^2/g$, such as those commonly used in lithium batteries, are suitable for Pt/C inks.

Furthermore, some embodiments use a blend of graphite and conductive carbon black in a platinum group metal/carbon composition in order to achieve high electrical conductivity and a good balance of electrode surface chemistry. A ratio of carbon black to graphite suitable for a platinum group metal/carbon ink composition is in the range of 0–5. Some embodiments are in the range of 0.2–1.

In some embodiments with metal powder the amount of graphite, conductive carbon, or mixtures thereof added to the composition based on solids is in the range of 62–85% by weight. In some embodiments with metallized graphite powder, the amount of graphite found in the composition, constituting the total amount of graphite found in the composition whether found as graphite supports, graphite conductive filler, or conductive carbon as described herein, is in a range of 62–85% by weight based on solids in the composition. In some embodiments the volume ratio of graphite/binder is in the range of 75/25 to 45/55.

(C) Poly(glycol Ether) Polymer

Poly(glycol ether) polymer additives are added to Pt/C ink composition to enhance the catalytic activity of platinum group metal catalysts toward electrocatalytic reaction of analytes. The multiple ether linkages in poly(glycol ether) (PGE), are effective in enhancing performance of Pt electrocatalyst and therefore enable the Pt/C working electrode to achieve high sensor performance at reduced metal catalyst loading. U.S. Pat. No. 5,616,222 to Maley et al disclosed the use of water-soluble poly(ethylene glycol)-based surfactants to enhance sensor signal intensity of platinum-carbon enzyme electrodes. A surfactant containing an oligomer of ethylene glycol, such as TRITON® X-100 (Union Carbide Corporation, Danbury, Conn.) may lead to high background current noise.

Poly(glycol ether) materials effective in enhancing electrocatalytic activity of platinum group metal-based sensors while minimizing background current include poly (tetramethylene glycol) (PTMEG) (such as TERATHANE® polyether glycol products from DuPont, Wilmington, Del.), poly(propylene glycol), and their derivatives. Derivatives of PGE include copolymers of glycol ether, alkyl or carboxylated poly(glycol ether), or polymers having PGE blocks on the polymer chain, such as polyurethane, acrylic polymers, and polyester, derived from PGE. Hydrophobic PGE, such as PTMEG and its derivatives, which offers a good balance of high sensor signal strength and low background current is suitable. Furthermore, the molecular weight of hydrophobic poly(glycol ether) suitable for the present invention can be in range of 200–5000. A suitable amount of PGE additives is in the range of 0.1–5% wt. based on total solids.

D. Thermoplastic Polymer

Thermoplastics are the polymeric binders used in the composition. Unlike PTF compositions with crosslinked binders, which require long curing time at high temperature, thermoplastic based PTF compositions can be used in a quick printing-drying process suitable for reel-to-reel sensor fabrication. Suitable thermoplastic binders provide a matrix that holds the electrocatalyst and graphite particles together and forms a coating with good scratch resistance and good adhesion to plastic film substrates. Thermoplastic polymers with a $T_g$>50° C. are suitable. Thermoplastic resins for use in the invention include polyacrylic, poly(styrene), styrene-containing acrylic copolymer, poly(acrylonitrile-butadiene-styrene), poly(hydroxyether), poly(ester), poly(carbonate), poly(imide). Thermoplastic polymers that contain no electrochemically active impurities, which contribute to background current noise, are suitable. Polymers that contain aromatic groups on the polymer chain or side chains are suitable. Examples are styrene-containing acrylic copolymers poly(styrene-acrylonitrile) (such as Tyril resins from Dow Chemicals, Midland, Mich.), benzyl methacrylate acrylic copolymer, poly(butadiene-acrylonitrile-styrene), poly(styrene), poly(hydroxyether) (such as UCAR phenoxy resins from Phenoxy Specialties, Rock Hill, S.C.), copolyester resins with tera-, iso- or phthalate aromatic groups (such as Vitel resins from Goodrich, Akron, Ohio), polycarbonate (such as Lexan resin from General Electric, Pittsfield, Mass.), and polyimide (such as Ultem resins from General Electric). The aromatic groups on the polymers enhance the wetting of the polymers on graphite surfaces, and thus reduce printing defects such as pin-holes caused by polymer de-wetting during printing and drying. The polymeric binders can be dissolved in solvents, or solvent blends to provide a vehicle for making metal-graphite compositions suitable for screen-printing.

In the dry electrode coating, an amount of binder in the range of 14–35% by weight based on solids is suitable. A lower binder level results in a porous coating, which has low scratch resistance and high background current. A higher binder level leads to low electrical conductivity and low electrocatalytic activity.

E. Solvent

A solvent suitable for the composition may have low electrochemical activity and inert to Pt-catalyzed chemical reactions. Most hydroxyl-containing organic solvents, such as alcohol or glycol alkyl ether can cause high background and auto-ignition with the electrocatalyst. Solvents, such as dibasic esters contain electrochemically active alcohol impurities. Solvents from the groups of alkyl and aryl ketones, aromatic hydrocarbon, glycol diacetates and glycol ether acetates or mixtures thereof are suitable solvents producing compositions with low sensor background current. Aromatic hydrocarbon solvents, which tend to have good wetting on graphite surfaces, impart a slightly shear thinning rheology on the composition and improve the printing of graphite based electrodes.

A typical Pt/C ink composition can be prepared as follows: (1) a polymeric binder solution is prepared by dissolving a thermoplastic polymer in a suitable solvent; (2) a dispersion of metal powder in the binder solution is then prepared by milling on a 3-roll mill; (3) a mixture of binder solution, metal powder dispersion, graphite and/or carbon black and metallized graphite, and solvent are mixed by high speed dispersion methods to make the PTF composition. The resultant composition typically has a viscosity in the range of 10–100 Pa.S and % solids of 10–40% suitable for screen printing. These ranges do not limit the scope of the invention.

Sensor Fabrication and Testing Criteria

An electrochemical sensor used for testing sensor performance of the composition of the present invention is based on a three-electrode design containing a working electrode, a counter electrode and a reference electrode. The working electrode is about a 1.3 cm$^2$ disk of the metal/graphite-carbon composition with 10–30 $\mu$m thickness. Both the counter electrode and the reference electrode are prints of a silver/silver chloride PTF composition as found in U.S. Pat. No. 5,851,438. The sensor is printed on a 5 mil polyester film substrate using a conventional screen printing process. Typically, the printing is done in a multiple print-dry sequence, which lays down conductive patterns of electrical contacts for measuring equipment attachments. Dielectric coatings are applied for protecting conductive lines. Electrochemical testing was done on custom-designed potentiostats.

Three key tests were performed: TEST A electrochemical sensor response to hydrogen peroxide, TEST B biosensor response to glucose, and TEST C electrochemical response to hydrogen peroxide on a smaller sensor. TEST A is done in a specially designed test cell which holds a 10 mil thick layer of test solution on top of the three-electrodes of the sensor and electrochemical response was monitored using a GMS module by Cygnus, Redwood City, Calif. The test cell is first filled with a phosphate buffered saline solution (PBS) having pH of 7.5, 0.1 M phosphate and 77 mM NaCl. The working electrode is preconditioned with the potential of the working electrode set against the reference electrode at 0.75V for 10 minutes and at 0.4V for 50 minutes, and the background current is recorded as the steady-state current measured between the working electrode and the counter electrode. Then the current response of the sensor after a $H_2O_2$ solution is injected in the test cell is recorded vs. time. A series of current measurements are made with different $H_2O_2$ concentrations. The slope of a linear plot of the current measured at a fixed time point, such as at 60 seconds, against the $H_2O_2$ concentration provides a measure of the sensor sensitivity to $H_2O_2$. A sensor sensitivity of 20–70 nA/cm$^2$·$\mu$M of $H_2O_2$ with background current noise in the range of 2–20 nA is acceptable. The preferred range is a sensor sensitivity of >50 nA/cm$^2$·$\mu$M of $H_2O_2$ with a background current noise of <5 nA.

TEST B is done using a GLUCOWATCH® by Cygnus, Redwood City, Calif. A biosensor, which has an enzyme-containing gel disk placed on top of the three electrodes of a printed electrochemical sensor. The gel disk contains a poly(ethylene oxide) gel, NaCl and phosphate buffer, and glucose oxidase enzyme for glucose oxidation and hydrogen peroxide generation. The biosensor is pre-conditioned with the working electrode on a 0.77V bias for 10 minutes followed by a 0.42V bias for 50 minutes, and the steady-state current measured at the end is the background current. Then 10 microliter volume of a 0.2 mM glucose solution sample is added to the gel. The current response is recorded verses time. The charge/electron response at time (t) from the glucose sample can be calculated by integrating over time (t) the current response minus the background current. The charge response at time (t) divided by the theoretical total charge generated from the glucose sample gives the % charge response (% recovery) recovered by the biosensor at time 2.5 minute provides a measure of the sensitivity of the biosensor to glucose. Glucose recovery >20% at 2.5 minute recovery time were acceptable results, but more preferred is >30% at 2.5 minute recovery time.

TEST C is done on a printed sensor with a working electrode having an area of about 4 mm$^2$ and Ag/AgCl reference and counter electrodes. This electrode is suitable for measuring much high concentrations of hydrogen peroxide than the sensor described above. When combined with an enzyme layer, this sensor can be used to measure glucose concentration in blood. The sensor is kept open to the air throughout the test. A drop of PBS buffer is place on the electrode to cover the working, counter, and reference electrodes. As in TEST A, the working electrode is preconditioned with the potential of the working electrode set against the reference electrode at 0.75V for 10 minutes and at 0.4V for 50 minutes, and the background current is recorded as the steady-state current measured between the working electrode and the counter electrode. After preconditioning, the buffer is removed. Then a 30 $\mu$L spike of $H_2O_2$ solution is placed to cover all three electrodes and the current response of the sensor is recorded vs. time. A series of current measurements are made with different $H_2O_2$ concentrations. The slope of a linear plot of the peak current, which occurs immediately, against the $H_2O_2$ concentration provides a measure of the sensor sensitivity to $H_2O_2$. FIG. 1 shows this plot for Examples 1, 2, and 4.

The present invention will be described in further detail by giving practical examples. The scope of the present invention, however, is not limited in any way by these practical examples. The stated test results do not limit the scope of the invention in any way.

INTERMEDIATES

The following formulations were used in the Examples:

Polymer Solution (A)

Prepared by dissolving 25 parts of poly(styrene-acrylonitrile) in 75 parts of ethylene glycol diacetate (Eastman Chemicals, TN).

Platinum Dispersion (B)

Prepared by milling on a three-roll mill a mixture containing 42 parts of Polymer Solution (A), 24.67 parts of ethylene glycol diacetate and 33.33 parts of platinum black (Colonial Metals Inc., MD). Scanning Electron Microgram (SEM) of a dried coating of Dispersion (B) showed that Pt particles were typically 0.5 μm in size.

Platinum Dispersion (C)

Prepared by milling on a three-roll mill of a mixture containing 28.6 parts of poly(tetramethylene glycol), 28.6 parts aromatic hydrocarbon 150 (Exxon, TX) and 42.8 parts platinum black. SEM of a dried coating of Platinum Dispersion (C) showed that Pt particles were <100 nm in size.

Iridium Dispersion (D)

Prepared by milling on a three-roll mill of a mixture containing 19 parts of Polymer Solution (A), 6 parts of ethylene glycol diacetate and 17 parts of iridium black (Colonial Metals Inc., MD), which had been treated with sodium hypophosphite as described for modified graphite.

PTMEG Solution (E)

Prepared by dissolving 2 parts TERATHANE® 2000 polyether glycol in 1 part aromatic hydrocarbon 150.

EXAMPLES

Example 1

A Pt/C composition having a Pt/(graphite+carbon) ratio of 2.5/97.5 was prepared with platinum black, PTMEG, graphite (Timrex SFG-15, Timcal, OH) and conductive carbon black (Super P with surface area of 60 m²/g from MMM Carbon, Belgium). The composition was prepared by mixing 10 parts of Polymer Solution (A), 36 parts of ethylene glycol diacetate, 2.0 parts of aromatic hydrocarbon 150, 3.4 parts of graphite, 3.0 parts of carbon black and 0.38 parts of Platinum Dispersion (C). Printed sensors of this Pt/C ink was tested for sensor performance. TEST A resulted in a sensitivity of 50–53 $nA/cm^2 \cdot \mu M$ $H_2O_2$ and background of 8–10 nA. TEST B resulted in a glucose % recovery of 54–56% at 24C and 70–76% at 32C, a background current of 63–67 nA at 24C and 92–105 nA at 32C. TEST C resulted in a sensitivity of 59 $nA/cm^2 \cdot \mu M$ $H_2O_2$ and a background of 2 nA. Results for test C are plotted in FIG. 1. The net paste composition was as follows:

| Ingredient | Weight Percent |
| --- | --- |
| Platinum black | 0.30 |
| PTMEG | 0.20 |
| Graphite | 6.2 |
| Carbon black | 5.5 |
| Poly(styrene-acrylonitrile) | 4.6 |
| Ethylene glycol diacetate | 79.4 |
| Aromatic hydrocarbon 150 | 3.8 |

Example 2

A Pt/C composition having a Pt/(graphite+carbon) ratio of 1/99 was prepared in the same way as Example 1. The composition was prepared by mixing 0.15 part of PTMEG and 46 parts of a Pt/C mixture. The Pt/C mixture contained 24.6 parts of Polymer Solution (A), 50 parts of ethylene glycol diacetate, 4 parts of aromatic hydrocarbon 150, 7.73 parts of graphite, 5.07 parts of carbon black and 0.293 parts of Platinum Dispersion (C). TEST A resulted in a sensitivity of 40 $nA/cm^2 \cdot \mu M$ $H_2O_2$ and a background current of 12 nA. TEST B resulted in a glucose recovery of 43% and a background of 53–56 nA. TEST C resulted in a sensitivity of 19 $nA/cm^2 \cdot \mu M$ $H_2O_2$ and a background of 2 nA. The net paste composition was as follows:

| Ingredient | Weight Percent |
| --- | --- |
| Platinum black | 0.14 |
| PTMEG | 0.40 |
| Graphite | 8.43 |
| Carbon black | 5.53 |
| Poly(styrene-acrylonitrile) | 6.71 |
| Ethylene glycol diacetate | 74.4 |
| Aromatic hydrocarbon 150 | 4.4 |

Example 3

A Pt/C composition similar to Example 1 except having a Pt/(graphite+carbon) Ratio of 1.5/98.5 was prepared and tested in the same way as above. TEST A resulted in a sensitivity of 38–45 $nA/cm^2 \cdot \mu M$ and a background current of 3–6 nA. TEST B resulted in a glucose recovery of 55–51% and background current of 59–71 nA. The net paste composition was as follows:

| Ingredient | Weight Percent |
| --- | --- |
| Platinum black | 0.18 |
| PTMEG | 0.12 |
| Graphite | 6.0 |
| Carbon black | 5.3 |
| Poly(styrene-acrylonitrile) | 4.4 |
| Ethylene glycol diacetate | 80.5 |
| Aromatic hydrocarbon 150 | 3.5 |

Example 4

To demonstrate the effectiveness of PTMEG in enhancing sensor performance for glucose and $H_2O_2$ sensing, a Pt/C composition similar to Example 1 without PTMEG was prepared and tested for comparison. The sample contains 12.3 parts of Polymer Solution (A), 36 parts ethylene glycol diacetate, 2 parts aromatic hydrocarbon 150, 3.4 parts graphite powder, 3.0 parts carbon black and 0.40 part Platinum Dispersion (B). TEST A resulted in a sensitivity of 2 nA/cm$^2$·$\mu$M H$_2$O$_2$ TEST B resulted in a glucose recovery of 3.7–3.9% and a background signal of 18–19 nA. Comparison of test results vs. those for Examples 1 and 2 clearly shows the effect of added PTMEG in enhancing sensor performance of Pt/C compositions. TEST C resulted in a sensitivity of 0 nA/cm$^2$·$\mu$M H$_2$O$_2$ and a background of 0–1 nA. Results for Test C are plotted in FIG. 1. The net paste composition was as follows:

| Ingredient | Weight Percent |
|---|---|
| Platinum black | 0.23 |
| Graphite | 5.95 |
| Carbon black | 5.25 |
| Poly(styrene-acrylonitrile) | 5.67 |
| Ethylene glycol diacetate | 79.4 |
| Aromatic hydrocarbon 150 | 3.5 |

Example 5

A Pt/C composition similar to Example 1 with TRITON® X-100 (oligomer of ethylene glycol) replacing PTMEG was prepared and tested for comparison. The composition was prepared by mixing 0.10 part of TRITON® X-100 and 50.0 parts of a Pt/C composition, which contained 64.1 parts of Polymer Solution (A), 141 parts of ethylene glycol diacetate, 6 parts of aromatic hydrocarbon 150, 74.4 parts of graphite and 12.0 parts of Platinum Dispersion (B). TEST A resulted in a sensitivity of 25–26 nA/cm$^2$·$\mu$M H$_2$O$_2$ and a background of 4 nA. TEST B resulted in a glucose recovery of 40% and a background current noise of 310 nA. Test results show Pt/C composition with a poly(ethylene glycol) oligomer based surfactant yielded high background current noise. The net paste composition was as follows:

| Ingredient | Weight Percent |
|---|---|
| TRITON ® X-100 | 0.20 |
| Platinum black | 1.3 |
| Graphite | 25.0 |
| Poly(styrene-acrylonitrile) | 5.8 |
| Ethylene glycol diacetate | 65.7 |
| Aromatic hydrocarbon 150 | 2.0 |

Example 6

This example shows that a Pt/C composition having a platinized graphite supported catalyst instead of a platinum black is effective in glucose sensing. The composition has a 4% Pt platinized graphite as the catalyst and a conductive filler blend having a graphite/carbon black ratio of 41/59, a Pt/filler ratio of 1.7/98.3. The composition was prepared by mixing 0.14 parts of PTMEG, 10 parts of Polymer Solution A, 68 parts of ethylene glycol diacetate, 2 parts of aromatic hydrocarbon, 3.6 parts of 4% platinized graphite, and 5.0 parts of carbon black. TEST A resulted in a sensitivity of 48–49 nA/cm$^2$·$\mu$M H$_2$O$_2$ and a background of 25–31 nA. TEST B resulted in a glucose recovery of 58% and a background of 52–55 nA. The net paste composition was as follows:

| Ingredient | Weight percent |
|---|---|
| PTMEG | 0.16 |
| 4% platinized graphite | 4.06 |
| Carbon black | 5.63 |
| Poly(styrene-acrylonitrile) | 2.82 |
| Ethylene glycol diacetate | 85.08 |
| Aromatic hydrocarbon | 2.25 |

Example 7

A Pt/C composition having PTMEG, platinized graphite and carbon black with a Pt/(graphite+carbon) ratio of 1/99. The composition contained 0.14 parts of TERATHANE® 2000 polyether glycol, 10 parts of Polymer Solution A, 75 parts of ethylene glycol diacetate, 12 parts of aromatic hydrocarbon 150, 1.8 parts of 5% Pt-graphite, and 6.8 parts of carbon black. TEST A resulted in a sensitivity of 27–29 nA/cm$^2$·$\mu$M H$_2$O$_2$ and a background of 6–8 nA. TEST B resulted in a glucose % recovery of 55–59% and a background of 71–108 nA. The net paste composition was as follows:

| Ingredient | Weight percent |
|---|---|
| PTMEG | 0.13 |
| 5% Pt-graphite | 1.70 |
| Carbon black | 6.43 |
| Poly(styrene-acrylonitrile) | 2.36 |
| Ethylene glycol diacetate | 78.03 |
| Aromatic hydrocarbon | 11.35 |

Example 8

A Pt/C composition having platinized graphite, graphite and PTMEG but no carbon black was prepared in the same way as Example 4. The composition contained 0.10 parts of PTMEG, 11.5 parts of Polymer Solution A, 27 parts of ethylene glycol diacetate, 1 part of aromatic hydrocarbon, 2.6 parts of 5% Pt-graphite, and 10.3 parts of SFG-15 graphite. TEST A resulted in a sensitivity of 20–26 nA/cm$^2$·$\mu$M H$_2$O$_2$ and background of 3–4 nA. TEST B resulted in a glucose recovery of 39–41% and a background of 48–49 nA. The net paste composition was as follows:

| Ingredient | Weight percent |
|---|---|
| PTMEG | 0.19 |
| 5% Pt-graphite | 4.95 |
| Graphite | 19.62 |
| Poly(styrene-acrylonitrile) | 5.48 |
| Ethylene glycol diacetate | 67.86 |
| Aromatic hydrocarbon | 1.90 |

Example 9

A composition similar to Example 8 was prepared without PTMEG additive. The composition contained 53.5 parts of Polymer Solution A, 127 parts of ethylene glycol diacetate, 5 parts of aromatic hydrocarbon, 12.9 parts of 5% platinized graphite, and 51.6 parts of graphite. TEST A resulted in a sensitivity of 12 nA/cm$^2$·$\mu$M H$_2$O$_2$ and a background of 3–4 nA. TEST B resulted in a glucose recovery of 14–15% and a background of 26–29 nA. Test results show that Pt/C without PTMEG yielded lower sensitivity and low glucose recovery in comparison with those for PTMEG-containing Pt/C composition in Example 8. The net paste composition was as follows:

| Ingredient | Weight percent |
| --- | --- |
| 5% Pt-graphite | 5.16 |
| Graphite | 20.64 |
| Poly(styrene-acrylonitrile) | 5.35 |
| Ethylene glycol diacetate | 66.85 |
| Aromatic hydrocarbon | 2.00 |

Example 10

This composition used a high surface area carbon (Vulcan XR-72, Cabot, MA) which requires three-roll milling for sufficient dispersion. A mixture containing 0.4 parts of PTMEG, 30 parts of Polymer Solution A, 60 parts of ethylene glycol diacetate, 2 parts of aromatic hydrocarbon, and 20.2 parts of high surface area carbon was milled on a 3-roll mill to disperse the carbon black. 100.9 parts of this mixture was then added to 5 parts of 5% platinized graphite, and 2 parts of ethylene glycol diacetate. TEST A resulted in a sensitivity of 2.2–2.5 nA/cm$^2$·$\mu$M H$_2$O$_2$. TEST B resulted in a glucose recovery of 41–42% and a background of 73–75 nA. The net paste composition was as follows:

| Ingredient | Weight percent |
| --- | --- |
| PTMEG | 0.33 |
| 5% platinized graphite | 4.63 |
| High SA carbon black | 16.78 |
| Poly(styrene-acrylonitrile) | 6.23 |
| Ethylene glycol diacetate | 70.37 |
| Aromatic hydrocarbon | 1.66 |

Example 11

This composition used iridium black as the platinum group metal. The composition was prepared by mixing 0.40 part of CARBOWAX® methoxypoly(ethylene glycol) 750 (Union Carbide, Danbury, Conn.) and 40.0 parts of an Ir/C composition, which contained 53.6 parts of Polymer Solution (A), 115.0 parts of ethylene glycol diacetate, 5.0 parts of aromatic hydrocarbon 150, 62.2 parts of graphite and 10.0 parts of Iridium Dispersion (D). TEST A resulted in a sensitivity of 29–33 nA/cm$^2$·$\mu$M H$_2$O$_2$ and a background of 5–8 nA. TEST B resulted in a glucose recovery of 22% and a background of 55–63 nA. The net paste composition was as follows:

| Ingredient | Weight Percent |
| --- | --- |
| Methoxypoly(ethylene glycol) | 0.99 |
| Iridium black | 1.63 |
| Graphite | 24.99 |
| Poly(styrene-acrylonitrile) | 5.86 |
| Ethylene glycol diacetate | 64.51 |
| Aromatic hydrocarbon 150 | 2.02 |

What is claimed is:

1. A composition consisting essentially of:
   (a) electrocatalyst selected from the group consisting of (1) platinum black and platinum group metal powders, alloys and mixtures thereof; (2) platinum group metals, alloys or mixtures thereof deposited on graphite support particles; or (3) mixtures of (1) and (2) wherein the surface area of said electrocatalyst is less than 150 m$^2$/g;
   (b) carbon-based electrically conductive filler selected from the group consisting of graphite and mixtures of graphite and conductive carbon black;
   (c) a hydrophobic poly(glycol ether) material selected from the group consisting of a hydrophobic poly(glycol ethers)polymer, poly(tetramethylene glycol), poly(propylene glycol), hydrophobic copolymers of poly(gycol ether) with alkyl and carboxylated poly(glycol ether) and mixtures thereof; and
   (d) a thermoplastic polymer material; and;
   (e) an aromatic hydrocarbon solvent.

2. The composition of claim 1 wherein the amount of electrocatalyst is in the range of 0.1–5% wt. based on solids in the composition.

3. The composition of claim 1 wherein the platinum group metal powder has a surface area >5 m$^2$/g.

4. The composition of claim 1 wherein the electrocatalyst is platinum black.

5. The composition of claim 4 wherein the platinum black has a surface area of 25–60 m$^2$/g.

6. The composition of claim 1 wherein the carbon-based conductive filler consists of mixtures of graphite and conductive carbon black having a ratio of carbon black to graphite that is in the range of 5/95 to 0.5/99.5.

7. The composition of claim 6 wherein the carbon black has an average primary particle size <100 nm.

8. The composition of claim 6 wherein the graphite is synthetic graphite, natural graphite or mixtures thereof having an average particle size >1 micron.

9. The composition of claim 1 wherein the platinum group metals, alloys, or mixtures thereof deposited on graphite support particles comprise 0.5–10% metal based on the weight of the particle.

10. The composition of claim 1 wherein the carbon-based conductive filler is in the range of 62–85% wt. based on solids in the composition.

11. The composition of claim 1 wherein the amount of hydrophobic poly(glycol ether) material is in the range of 0.1–5% wt. based on solids in the composition.

12. The composition of claim 1 wherein the amount of thermoplastic polymer is in the range of 14–35% wt. based on solids in the composition.

13. The composition of claim 1 wherein the thermoplastic polymer a has T$_g$>50° C.

14. The composition of claim 1 wherein the thermoplastic polymer is selected from poly(styrene), styrene-containing acrylic copolymer, poly(acrylonitrile-butadiene styrene), poly(hydroxyether), polyester, poly(carbonate), polyimide, and mixtures thereof.

15. A disposable biosensor comprising the composition of claim 1.

16. A process for dispersing platinum group metal powders, alloys, or mixtures thereof, wherein the surface area of said platinum group metal powders, alloys or mixtures thereof is less than 65 m$^2$/g, comprising the steps of first mixing an electrocatalyst selected from the group consisting of (1) platinum black and platinum group metal powders, alloys and mixtures thereof; (2) platinum group metals, alloys or mixtures thereof deposited on graphite support particles; or (3) mixtures of (1) and (2) wherein the surface area of said electrocatalyst is less than 150 m²/g with; a hydrophobic poly(glycol ether) material dissolved in an aromatic hydrocarbon solvent wherein the hydrophobic poly(glycol ether) material selected from the group consisting of a hydrophobic poly(glycol ethers) polymer, poly (tetramethylene glycol), poly(propylene glycol), hydrophobic copolymers of poly(gycol ether) with alkyl and carboxylated poly(glycol ether) and mixtures thereof, and using a dispersing means to acheive a desired particle size.

17. The process of claim 16 wherein the dispersing means a three-roll-mill.

* * * * *